United States Patent [19]
Kropke et al.

[11] Patent Number: 5,639,797
[45] Date of Patent: Jun. 17, 1997

[54] WATER-IN-OIL EMULSIONS CONTAINING WATER-SOLUBLE ALKYL GLYCOSIDES

[75] Inventors: Rainer Kropke, Marschacht; Wolfgang Pape; Gunther Schneider, both of Hamburg; Wilhelm Stahl, Frankfurt; Matthias Wiesner, Mainz, all of Germany

[73] Assignees: Beiersdorf Aktiengesellschaft, Hamburg; Hoechst Aktiengesellschaft, Frankfurt am Main, both of Germany

[21] Appl. No.: 387,877
[22] PCT Filed: Sep. 13, 1993
[86] PCT No.: PCT/EP93/02465
§ 371 Date: Feb. 22, 1995
§ 102(e) Date: Feb. 22, 1995
[87] PCT Pub. No.: WO94/06408
PCT Pub. Date: Mar. 31, 1994

[30] Foreign Application Priority Data

Sep. 15, 1992 [DE] Germany .................. 42 30 504.7

[51] Int. Cl.$^6$ .................................................. A61K 7/42
[52] U.S. Cl. ............... 424/78.03; 424/59; 424/78.02; 514/844; 514/846; 514/847; 514/937; 514/938
[58] Field of Search .................... 514/844, 846, 514/847, 937, 938; 424/78.03, 78.02, 59

[56] References Cited

FOREIGN PATENT DOCUMENTS

| 0458600 | 5/1991 | European Pat. Off. . |
| 9202594 | 2/1992 | WIPO . |

*Primary Examiner*—Terressa Mosley
*Attorney, Agent, or Firm*—Sprung Horn Kramer & Woods

[57] ABSTRACT

A W/O emulsion comprising water, oil and at least one water-soluble alkyl glycoside. Cosmetic and dermatological skincare composition, based thereon are easier to prepare, of lower viscosity and improved stability.

10 Claims, No Drawings

WATER-IN-OIL EMULSIONS CONTAINING WATER-SOLUBLE ALKYL GLYCOSIDES

The present invention relates to stable cosmetic compositions, in particular water-in-oil emulsions (W/O emulsions), which are protected against physical decomposition.

Skincare in the context of the invention is primarily to be understood as meaning intensifying, assisting and, if necessary, re-establishing the natural function of the skin as a barrier against environmental influences (for example dirt, foreign substances and microorganisms) and against the loss of endogenous substances (for example water, electrolytes and natural moisture-binding substances).

If the natural function of the skin is disturbed, increased absorption of toxic and/or allergenic foreign substances or attack by pathogenic microorganisms and, as a consequence, inflammatory or allergic skin reactions may occur.

The human skin constantly loses a certain amount of moisture by endogenous mechanisms, as it does by transpiration. However, the skin also loses important functional constituents due to external influences, such as daily washing of the body, wind and weather. Although healthy skin is entirely capable of compensating this loss, the aim of skincare is to assist the skin in compensating this loss. However, precisely when the natural regeneration capacity is inadequate, for example due to severe stress or even an illness, regulation of skin moisture and other relevant contents is essential.

The aim of skincare is thus to re-establish and promote a normal functional profile of the skin and integumentary appendages.

The following methods of skincare are known per se:

a) Occlusion of the Skin

If the skin is covered with a film of lipid or lipid/water (conventional ointments or creams), the barrier function of the skin is not re-established directly. The lipid film is an external physical protective layer.

b) Treatment of the Skin With Essential Fatty Acids

Essential fatty acids are currently occasionally employed in dermatological preparations for treatment of dry skin.

c) Treatment of the skin with substances having a keratolytic action (for example urea, salicylic acid and the like). These substances have a keratolytic, proteolytic, penetration-promoting, epidermis-thinning, antipruritic or water-binding action, depending on their nature and the concentration used. Their use is essentially limited to medical indications.

d) Treatment with moisture-regulating substances (for example glycerol, sorbitol and the like). The group of these substances is of particular interest, since it includes many representatives which have a good action. Nevertheless, a disadvantage is that most of these substances either are expensive or can be incorporated into cosmetic formulations only under complicated conditions. The statements under point c) furthermore apply to some representatives of this group.

Skincare cosmetic formulations include, in particular, cosmetic emulsions, that is to say W/O emulsions.

Emulsions of this type can on the one hand be employed without an active compound, a good action in general already being achieved, but on the other hand emulsions containing active compounds are being used more and more. It was thus an object of the present invention to provide W/O emulsions which both can function as a vehicle for active compounds of the most diverse types and also have outstanding dermatological properties without an active compound.

A disadvantage of many water-in-oil emulsions of the prior art is furthermore that they are not stable towards physical decomposition. The undesirable behaviour which occurs the most frequently is usually called "oiling out". This means that the aqueous phase and oily phase gradually separate. This manifests itself, for example, in drops of oil emerging from a W/O cream (=water-in-oil cream). However, once an emulsion has started to decompose, this process cannot be reversed again by simple means. At least, such means are not available to the user.

W/O emulsions are particularly sensitive towards a content of highly surface-active substances, the water-solubility of which is high, in contrast to emulsifiers, the fat-solubility of which is high.

W/O emulsions have hitherto always been destroyed by addition of highly surface-active substances of the prior art, this having manifested itself in phase separation.

The object of the present invention was thus to eliminate all the disadvantages of the prior art. In particular, stable skincare W/O emulsions were to be provided.

It has been found, surprisingly, and therein lies the achievement of the object, that W/O emulsions comprising a water-soluble alkyl glycoside or a mixture of several water-soluble alkyl glycosides remedy the disadvantages of the prior art.

The alkyl glycosides according to the invention are distinguished by the structure

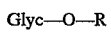

in which R, the aglycon, is a branched or unbranched alkyl radical having 5–18 carbon atoms, preferably an unbranched alkyl radical having 8–10 carbon atoms.

According to the invention, Glyc is a monosaccharidic sugar residue which is linked glycosidically with the aglycon R.

Advantageous embodiments of the present invention exist if Glyc is chosen from the group consisting of hexosyl residues, that is to say, for example, glucosyl, mannosyl, galactosyl and fructosyl.

It is essential to the invention in all cases that the alkyl glycosides chosen are readily water-soluble.

Preferred embodiments of the present invention are W/O emulsions comprising an alkyl glucosides or a mixture of several alkyl glucosides, that is to say those glycosides in which Glyc is a glucosyl radical.

Alkyl glucosides are distinguished by the structure

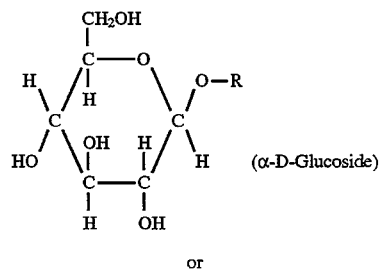

or

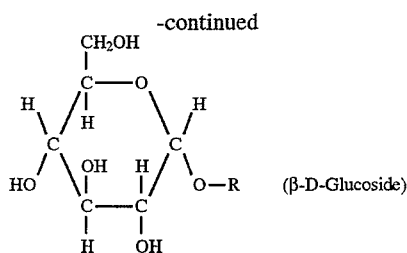

(β-D-Glucoside)

R is a branched or unbranched alkyl radical having 5–14 carbon atoms, preferably an unbranched alkyl radical having 8–10 carbon atoms.

Although the alkyl glucosides according to the invention can advantageously be chosen per se both from α-D-glucosides and from β-D-glucosides, the β-D-glucosides (or their mirror image forms, which are, however, less readily accessible) are preferred. This is based on the fact that the α-D-glucosides in general have a poorer water-solubility than the β-D-glucosides.

The alkyl glucosides are particularly advantageously distinguished by the following structures:

which would also lead to W/O emulsions without addition of the alkyl glycosides according to the invention.

Without alkyl glycosides, however, W/O emulsions are obtained which have a lower stability, have a cosmetic elegance which leaves something to be desired, which are more viscous than smooth and which have a less pronounced skincare action. Furthermore, such W/O emulsions are less suitable as a vehicle for active compounds.

The alkyl glycosides thus improve the properties of the W/O emulsion, hut are themselves not W/O emulsifiers.

It was furthermore astonishing that a significantly improved start of the emulsion formation is to be observed by using the alkyl glycosides according to the invention. This is to be understood as meaning immediate formation of an emulsion after the corresponding fatty and aqueous phases have been brought together.

Furthermore, compared with batches without the alkyl glycosides according to the invention, the viscosity of the resulting W/O emulsions is significantly reduced, the consistency is noticeably improved and the tendency of the emulsion to oil out, that is to say to separate into an aqueous and an oily phase, is considerably reduced.

It is of course known to the expert that high-quality cosmetic compositions are usually inconceivable without

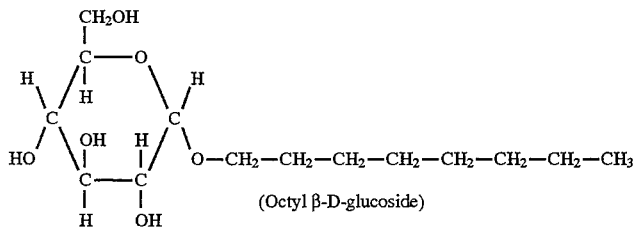

(Octyl β-D-glucoside)

and

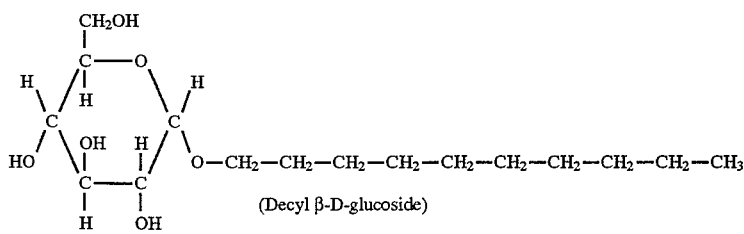

(Decyl β-D-glucoside)

The emulsions according to the invention preferably comprise up to 0.5% by weight of alkyl glycosides, advantageously alkyl glucosides, preferably up to 0.3% by weight, in each case based on the total weight of the W/O emulsion. Concentrations of 0.001 to 0.20% by weight, based on the total weight of the W/O emulsion, are especially preferably employed.

In particular, it is also advantageous to chose the concentration of the alkyl glycosides according to the invention such that it is smaller than the particular critical micelle formation concentration (CMC).

Since alkyl glycosides belong to the highly surface-active substances, it was astonishing that an addition of alkyl glycosides to W/O emulsions
would be stable,
would lead to emulsions which, cosmetically, are of particularly high quality,
would lead to particularly smooth emulsions,
would lead to emulsions having a particularly pronounced skincare action,
would lead to vehicles for many types of active compounds.

The W/O emulsions according to the invention obligatorily comprise a W/O emulsifier or an emulsifier mixture the customary auxiliaries and additives. These include, for example, consistency agents, fillers, perfume, dyestuffs, emulsifiers, additional active compounds such as vitamins or proteins, light protection agents, stabilizers, antioxidants, insect repellents, alcohol, water, salts, antimicrobial, proteolytic or keratolytic substances and the like.

Depending on their build-up, the compositions according to the invention can accordingly be used, for example, as skin protection cream, cleansing milk, sunscreen lotion, nutrient cream, day or night cream and the like. Where appropriate, it is possible and advantageous to use the compositions according to the invention as a base for pharmaceutical formulations.

The invention also relates to the use of the W/O emulsions described as cosmetic and/or dermatological skincare compositions. The W/O emulsions according to the invention are advantageously prepared by introducing the alkyl glycoside or alkyl glycosides and the other water-soluble components into the aqueous phase, introducing the oil-soluble components into the fatty phase and combining and then homogenizing the aqueous phase and the oily phase with one another at a temperature at which both phases are in the liquid form.

The invention thus also relates to a process for the preparation of the W/O emulsions described, characterized in that the water-soluble alkyl glycoside or water-soluble alkyl glucosides and the other water-soluble components are introduced into the aqueous phase, the oil-soluble components are introduced into the fatty phase and the aqueous phase and the oily phase are combined and then homogenized with one another at a temperature at which both phases are in the liquid form.

However, it is particularly advantageous to carry out processes for the preparation of W/O emulsions according to the invention which proceed in accordance with the hot/cold technique. This means that one of the phases to be combined (preferably the aqueous phase) is at room temperature, while the other phase (preferably the fatty phase) is at higher temperatures, in particular at temperatures at which all the solid constituents of the phase in question are in liquid or dissolved form.

The invention therefore preferably relates to a process for the preparation of W/O emulsions according to the invention, characterized in that the water-soluble alkyl glycoside or the water-soluble alkyl glucosides and the other water-soluble components are introduced into the aqueous phase, the oil-soluble components are introduced into the fatty phase, the aqueous phase being at a temperature of between 15° and 35° C. and the oil phase being at a temperature at which all the solid constituents of the oily phase are in liquid or dissolved form, and the aqueous phase and the oily phase are combined with one another and then homogenized.

The advantage of this particularly preferred preparation process is that, because one phase can be essentially at room temperature, considerable amounts of energy can be saved during the preparation.

The following examples are intended to illustrate the invention in more detail, but without the intention of limiting the invention to these examples. Rather, on the basis of his or her expert knowledge, the expert is capable of making modifications which do not go beyond the scope of the present invention.

The amounts data in the examples relate to % by weight, based on the total composition.

EXAMPLE 1

|  | % by weight |
| --- | --- |
| Polyglyceryl 3-diisostearate | 2.50 |
| Paraffin wax | 3.00 |
| Paraffin oil DAB 9 | 10.00 |
| Cetearyl octanoate | 10.00 |
| Beeswax | 4.00 |
| Glycerol | 5.00 |
| Decyl β-D-glucoside | 0.01 |
| Perfume, preservative, additives | q.s. |
| Water | to 100.00 |

EXAMPLE 2

|  | % by weight |
| --- | --- |
| Cholesterol | 1.50 |
| Paraffin wax | 3.00 |
| Vaseline | 5.00 |
| Paraffin oil DAB 9 | 20.00 |
| Glycerol | .5.00 |
| Decyl β-D-glucoside | 0.01 |
| Perfume, preservative, additives | q.s. |
| Water | to 100.00 |

EXAMPLE 3

|  | % by weight |
| --- | --- |
| Wool wax alcohols | 2.50 |
| Paraffin wax | 6.00 |
| Beeswax | 1.00 |
| Vaseline | 3.00 |
| Paraffin oil DAB 9 | 20.00 |
| Glycerol | 5.00 |
| Decyl β-D-glucoside | 0.01 |
| Perfume, preservative, additives | q.s. |
| Water | to 100.00 |

EXAMPLE 4

|  | % by weight |
| --- | --- |
| Polyglyceryl 3-diisostearate | 2.50 |
| Paraffin wax | 3.00 |
| Paraffin oil DAB 9 | 10.00 |
| Cetearyloctanoate | 10.00 |
| Beeswax | 4.00 |
| Glycerol | 5.00 |
| Octyl β-D-glucoside | 0.05 |
| Perfume, preservative, additives | q.s. |
| Water | to 100.00 |

EXAMPLE 5

|  | % by weight |
| --- | --- |
| Cholesterol | 1.50 |
| Paraffin wax | 3.00 |
| Vaseline | 5.00 |
| Paraffin oil DAB 9 | 20.00 |
| Glycerol | 5.00 |
| Octyl β-D-glucoside | 0.05 |
| Perfume, preservative, additives | q.s. |
| Water | to 100.00 |

EXAMPLE 6

|  | % by weight |
| --- | --- |
| Wool wax alcohols | 2.50 |
| Paraffin wax | 6.00 |
| Beeswax | 1.00 |
| Vaseline | 3.00 |
| Paraffin oil DAB 9 | 20.00 |
| Glycerol | 5.00 |
| Decyl β-D-glucoside | 0.05 |
| Perfume, preservative, additives | q.s. |
| Water | to 100.00 |

EXAMPLE 7

|  | % by weight |
|---|---|
| Polyglyceryl 3-diisostearate | 1.50 |
| PEG 40 sorbitan heptaisostearate | 1.50 |
| Paraffin oil DAB 9 | 15.00 |
| Vaseline | 8.00 |
| Paraffin wax | 6.00 |
| 2-Octyldodecanol | 8.00 |
| Aluminium stearate | 0.20 |
| Glycerol | 5.00 |
| Decyl β-D-glucoside | 0.01 |
| Perfume, preservative, additives | q.s. |
| Water | to 100.00 |

EXAMPLE 8

|  | % by weight |
|---|---|
| Polyglyercyl 3-diisostearate | 1.50 |
| PEG 40 sorbitan heptaisostearate | 1.50 |
| Paraffin oil DAB 9 | 15.00 |
| Vaseline | 8.00 |
| Paraffin wax | 6.00 |
| 2-Octyldodecanol | 8.00 |
| Aluminium stearate | 0.20 |
| Glycerol | 5.00 |
| Octyl β-D-glucoside | 0.05 |
| Perfume, preservative, additives | q.s. |
| Water | to 100.00 |

EXAMPLE 9

|  | % by weight |
|---|---|
| Polyglyceryl 3-diisostearate | 2.50 |
| Paraffin wax | 3.00 |
| Paraffin oil DAB 9 | 10.00 |
| Cetearyl octanoate | 10.00 |
| Beeswax | 4.00 |
| Glycerol | 5.00 |
| Decyl β-D-glucoside | 0.003 |
| Perfume, preservative, additives | q.s. |
| Water | to 100.00 |

EXAMPLE 10

|  | % by weight |
|---|---|
| Cholesterol | 1.50 |
| Paraffin wax | 3.00 |
| Vaseline | 5.00 |
| Paraffin oil DAB 9 | 20.00 |
| Glycerol | 5.00 |
| Decyl β-D-glucoside | 0.003 |
| Perfume, preservative, additives | q.s. |
| Water | to 100.00 |

EXAMPLE 11

|  | % by weight |
|---|---|
| Wool wax alcohols | 2.50 |
| Paraffin wax | 6.00 |
| Beeswax | 1.00 |
| Vaseline | 3.00 |
| Paraffin oil DAB 9 | 20.00 |
| Glycerol | 5.00 |
| Decyl β-D-glucoside | 0.003 |
| Perfume, preservative, additives | q.s. |
| Water | to 100.00 |

EXAMPLE 12

|  | % by weight |
|---|---|
| Polyglyceryl 3-diisostearate | 2.50 |
| Paraffin wax | 3.00 |
| Paraffin oil DAB 9 | 10.00 |
| Cetearyl octanoate | 10.00 |
| Beeswax | 4.00 |
| Glycerol | 5.00 |
| Octyl β-D-glucoside | 0.005 |
| Perfume, preservative, additives | q.s. |
| Water | to 100.00 |

EXAMPLE 13

|  | % by weight |
|---|---|
| Cholesterol | 1.50 |
| Paraffin wax | 3.00 |
| Vaseline | 5.00 |
| Paraffin oil DAB 9 | 20.00 |
| Glycerol | 5.00 |
| Octyl β-D-glucoside | 0.005 |
| Perfume, preservative, additives | q.s. |
| Water | to 100.00 |

EXAMPLE 14

|  | % by weight |
|---|---|
| Wool wax alcohols | 2.50 |
| Paraffin wax | 6.00 |
| Beeswax | 1.00 |
| Vaseline | 3.00 |
| Paraffin oil DAB 9 | 20.00 |
| Glycerol | 5.00 |
| Decyl β-D-glucoside | 0.003 |
| Perfume, preservative, additives | q.s. |
| Water | to 100.00 |

EXAMPLE 15

|  | % by weight |
|---|---|
| Polygylceryl 3-diisostearate | 1.50 |
| PEG-40 sorbitan heptaisostearate | 1.50 |
| Paraffin oil DAB 9 | 15.00 |
| Vaseline | 8.00 |
| Paraffin wax | 6.00 |
| 2-Octyldodecanol | 8.00 |
| Aluminium stearate | 0.20 |
| Glycerol | 5.00 |
| Decyl β-D-glucoside | 0.003 |
| Perfume, preservative, additives | q.s. |
| Water | to 100.00 |

EXAMPLE 16

|  | % by weight |
| --- | --- |
| Polyglyceryl 3-diisostearate | 1.50 |
| PEG-40 sorbitan heptaisostearate | 1.50 |
| Paraffin oil DAB 9 | 15.00 |
| Vaseline | 8.00 |
| Paraffin wax | 6.00 |
| 2-Octyldodecanol | 8.00 |
| Aluminium stearate | 0.20 |
| Glycerol | 5.00 |
| Octyl-β-D-glucoside | 0.005 |
| Perfume, preservative, additives | q.s. |
| Water | to 100.00 |

COMPARISON EXPERIMENT 1

A W/O emulsion was prepared with the composition according to Example 11 by bringing together fatty phase: of wool wax alcohols, paraffin wax, beeswax, vaseline and paraffin oil DAB 9, temperature: 75° C. aqueous phase: glycerol, decyl β-D-glucoside, water (without perfume, preservative, additives), temperature: 75° C.

A smooth emulsion was formed immediately.

COMPARISON EXPERIMENT 2

A W/O emulsion according to Comparison Experiment 1 was prepared, with the only difference that no decyl β-glucoside was added. It took ten minutes for a viscous emulsion to be formed.

COMPARISON EXPERIMENT 3

A W/O emulsion was prepared with the composition according to Example 11, by bringing together fatty phase: of wool wax alcohols, paraffin wax, beeswax, vaseline and paraffin oil DAB 9, temperature: 75° C. aqueous phase: glycerol, decyl β-D-glucoside, water (without perfume, preservative, additives), temperature: 25° C.

A smooth emulsion was formed practically immediately.

COMPARISON EXPERIMENT 4

A W/O emulsion according to Comparison Experiment 3 was prepared, with the only difference that no decyl β-glucoside was added. It took about twenty minutes for an emulsion which was unstable and cosmetically unacceptable to be formed.

We claim:

1. A water-in-oil emulsion comprising water, oil and 0.001 to 0.20% by weight of a water-soluble alkyl glycoside or of a mixture of water-soluble alkyl glycosides.

2. A water-in-oil emulsion according to claim 1, wherein the water-soluble alkyl glycoside is an alkyl glucoside.

3. A water-in-oil emulsion according to claim 1, wherein the alkyl glucoside is at least one of

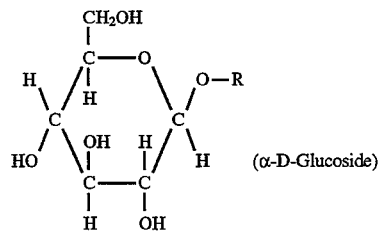

(α-D-Glucoside)

and

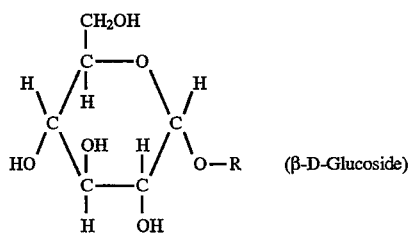

(β-D-Glucoside)

wherein

R is a branched or unbranched alkyl radical having 5–18 carbon atoms.

4. A water-in-oil emulsion according to claim 3, wherein the alkyl glucoside is of β-configuration and R is an unbranched alkyl radical of 8–10 carbon atoms.

5. A water-in-oil emulsion according to claim 1, wherein the alkyl glucoside is

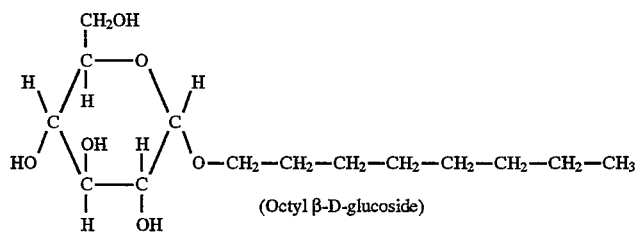

(Octyl β-D-glucoside)

or

-continued

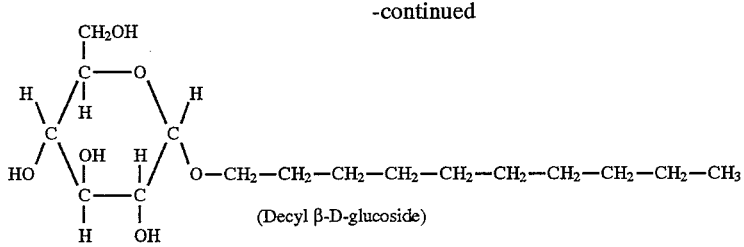

(Decyl β-D-glucoside)

6. A water-in-oil emulsion according to claim 1, wherein the alkyl glycoside is present in 0.3 to 0.5% based on the total weight of the W/O emulsion.

7. A water-in-oil emulsion according to claim 1, containing a cosmetic or dermatological skincare ingredient.

8. A low-viscosity water-in-oil emulsion according to claim 5, wherein the alkyl glycoside is present in 0.3 to 0.5% and a concentration of alkyl glycosides, in each case based on the total weight of the W/O emulsion, the emulsion further containing a cosmetic or dermatological skincare ingredient.

9. A process for the preparation of a water-in-oil emulsion according to claim 1, comprising introducing the water-soluble alkyl glycoside and any other water-soluble components into water to form an aqueous phase, combining oil-soluble components to form a fatty phase, combining the aqueous phase and the oily phase with one another, and homogenizing the mixture at a temperature at which both phases are in liquid form.

10. A process according to claim 9, wherein, when mixed, the water aqueous phase is at a temperature of between 15° and 35° C. and the oil phase is at a temperature at which all the solid constituents of the oily phase are in liquid or dissolved form.

* * * * *

UNITED STATES PATENT AND TRADEMARK OFFICE
CERTIFICATE OF CORRECTION

PATENT NO. : 5,639,797
DATED : June 17, 1997
INVENTOR(S) : Kropke, et al.

It is certified that error appears in the above-indentified patent and that said Letters Patent is hereby corrected as shown below:

Col. 11, line 20  Delete " in each case "

Signed and Sealed this

Seventeenth Day of February, 1998

Attest:

BRUCE LEHMAN

Attesting Officer   Commissioner of Patents and Trademarks